(12) United States Patent
Lee et al.

(10) Patent No.: US 9,514,416 B2
(45) Date of Patent: Dec. 6, 2016

(54) APPARATUS AND METHOD OF DIAGNOSING A LESION USING IMAGE DATA AND DIAGNOSTIC MODELS

(71) Applicant: Samsung Electronics Co., Ltd., Suwon-si (KR)

(72) Inventors: Jae-Cheol Lee, Seoul (KR); Yeong-Kyeong Seong, Yongin-si (KR); Ki-Yong Lee, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 277 days.

(21) Appl. No.: 14/041,112

(22) Filed: Sep. 30, 2013

(65) Prior Publication Data

US 2014/0101080 A1  Apr. 10, 2014

(30) Foreign Application Priority Data

Sep. 28, 2012 (KR) .................. 10-2012-0109401

(51) Int. Cl.
| | | |
|---|---|---|
| G06F 15/18 | (2006.01) | |
| G06N 99/00 | (2010.01) | |
| G06F 19/00 | (2011.01) | |

(52) U.S. Cl.
CPC .......... *G06N 99/005* (2013.01); *G06F 19/345* (2013.01); *G06F 19/3443* (2013.01); *G06K 2209/05* (2013.01)

(58) Field of Classification Search
USPC .............................................. 706/12, 45, 62
See application file for complete search history.

(56) References Cited

U.S. PATENT DOCUMENTS

| | | |
|---|---|---|
| 5,769,074 A | 6/1998 | Barnhill et al. |
| 6,748,044 B2 | 6/2004 | Sabol et al. |
| 2003/0174873 A1* | 9/2003 | Giger et al. ................. 382/128 |
| 2005/0071143 A1* | 3/2005 | Tran ...................... G06F 19/325 703/11 |
| 2006/0089824 A1* | 4/2006 | Siekmeier et al. ............. 703/11 |
| 2007/0133852 A1* | 6/2007 | Collins et al. ................ 382/128 |
| 2008/0145841 A1* | 6/2008 | Libutti et al. ..................... 435/6 |
| 2009/0006061 A1 | 1/2009 | Thukral et al. |
| 2009/0125463 A1 | 5/2009 | Hido |
| 2009/0222248 A1* | 9/2009 | Grichnik ............... G06F 19/345 703/11 |
| 2009/0233279 A1* | 9/2009 | Glinskii ........................... 435/6 |
| 2009/0259494 A1* | 10/2009 | Feder et al. ..................... 705/3 |
| 2010/0070188 A1* | 3/2010 | Solomon ............. A61B 5/0031 702/19 |
| 2010/0158332 A1* | 6/2010 | Rico et al. ..................... 382/128 |
| 2011/0021451 A1* | 1/2011 | Wenk ............... G01N 33/57449 514/34 |
| 2011/0082712 A1* | 4/2011 | Eberhardt, III ..... G06F 19/3437 705/4 |
| 2011/0312520 A1* | 12/2011 | Kennedy et al. ................. 506/9 |
| 2012/0295815 A1* | 11/2012 | Lindahl ................ C12Q 1/6886 506/9 |
| 2013/0131992 A1* | 5/2013 | Wilkes ............... G01R 33/4625 702/19 |
| 2014/0016832 A1* | 1/2014 | Kong et al. ................... 382/115 |

FOREIGN PATENT DOCUMENTS

| | | |
|---|---|---|
| KR | 10-2010-0027165 A | 3/2010 |
| KR | 10-1144964 A | 5/2012 |

* cited by examiner

*Primary Examiner* — David Vincent
(74) *Attorney, Agent, or Firm* — Jefferson IP Law, LLP

(57) ABSTRACT

An apparatus and a method for diagnosis are provided. The apparatus for diagnosis lesion include: a model generation unit configured to categorize learning data into one or more categories and to generate one or more categorized diagnostic models based on the categorized learning data, a model selection unit configured to select one or more diagnostic model for diagnosing a lesion from the categorized diagnostic models, and a diagnosis unit configured to diagnose the lesion based on image data of the lesion and the selected one or more diagnostic model.

16 Claims, 13 Drawing Sheets

APPARATUS AND METHOD OF DIAGNOSING A LESION USING IMAGE DATA AND DIAGNOSTIC MODELS

CROSS-REFERENCE TO RELATED APPLICATION(S)

This application claims the benefit under 35 U.S.C. §119(a) of Korean Patent Application No. 10-2012-0109401, filed on Sep. 28, 2012, in the Korean Intellectual Property Office, the entire disclosure of which is incorporated herein by reference for all purposes.

BACKGROUND

1. Field

The following description relates to a computer-aided diagnostic technique, and to an apparatus and method for diagnosis that uses categorized diagnostic models.

2. Description of the Related Art

Computer-aided diagnosis (CAD) systems are diagnostic systems capable of reducing radiologists' workload by highlighting suspicious portions in a medical image based on the results of a quantitative analysis conducted by a computer so as to facilitate radiologists in making their final diagnoses. CAD systems use various algorithms to make diagnoses of lesions. Such algorithms establish a diagnostic model through the learning of a large amount of data and classify newly input data based on the established diagnostic model. Accordingly, the performance of a CAD system in classifying the input data highly depends on the established diagnostic model. It is thus desirable to generate a diagnostic model by collecting and learning as much data as possible. However, creating an accurate diagnostic model is still difficult. In general, the more data is collected, the more precise the diagnosis is likely to be. However, this holds true only for the case of lesions that are common among the studied population from which the learning data was collected. Some cases of lesions may be less common among the population from which the learning data was collected, and certain set of data may present lesions differently. Thus, it may still be hard to detect lesions with unusual shapes or features based on the learning data, even if the size of the learning data is large.

SUMMARY

In one general aspect, there is provided an apparatus for diagnosis, the apparatus including: a model generation unit configured to categorize learning data into one or more categories and to generate one or more categorized diagnostic models based on the categorized learning data; a model selection unit configured to select one or more diagnostic model for diagnosing a lesion from the categorized diagnostic models; and a diagnosis unit configured to diagnose the lesion based on image data of the lesion and the selected one or more diagnostic model.

The diagnosis unit may be configured to diagnose the lesion based on lesion feature values extracted from the image data and the selected one or more diagnostic model.

The quantitative analysis may involve extracting lesion feature values from the image data of the lesion based on the selected one or more diagnostic model.

The model generation unit may include: a data collection unit configured to collect the learning data from prior patients or medical database; a data categorization unit configured to categorize the learning data into the one or more categories according to a predefined set of rules; a model learning unit configured to generate the categorized diagnostic models by learning the categorized learning data; and a model storage unit configured to store the categorized diagnostic models.

The data categorization unit may be further configured to categorize the learning data based on at least one of patient information regarding each patient, medical institution information that made diagnoses, and imaging device information on imaging devices used to acquire diagnostic images.

The model selection unit may include: a model selection unit configured to allow a user to select one of an automatic recommendation mode, a user selection mode and an integrated mode; a model recommendation unit configured to, in response to the automatic recommendation mode being selected, analyze patient information or image data of patient, automatically determine one or more diagnostic models to apply to diagnose the lesion, and display the determined diagnostic models; a user selection unit configured to, in response to the user selection mode being selected, allow the user to select at least one of the displayed diagnostic models; and an integration unit configured to, in response to the integrated mode being selected, control both the model recommendation unit and the user selection unit to execute the automatic recommendation mode and the user selection mode, respectively.

The general aspect of the apparatus may further include: an integrated model generation unit configured to generate an integrated diagnostic model based on the selected one or more diagnostic model.

The diagnosis unit may be further configured to, in response to the model selection unit diagnosing the lesion of the patient based on each of the selected diagnostic models, calculate and display model-by-model diagnosis result data based on the diagnosis and calculate and display integrated diagnosis result data through integration of the model-by-model diagnosis result data, the integrated diagnosis result data displaying a probability that the lesion is benign or malignant.

The diagnosis unit may be further configured to calculate and display the integrated diagnosis result data in consideration of preferences among the selected diagnostic models.

In another general aspect, there is provided a method for diagnosis, the method involving: categorizing learning data into one or more categories and generating one or more categorized diagnostic models based on the categorized learning data; selecting one or more diagnostic model for diagnosing a lesion from the categorized diagnostic models; and diagnosing the lesion based on image data of the lesion and the selected one or more diagnostic model.

The diagnosing of the lesion may involve diagnosing the lesion based on lesion feature values extracted from the image data and the selected one or more diagnostic model.

The generating of the categorized diagnostic models may involve: collecting the learning data from prior patients or medical database; categorizing the learning data into the one or more categories according to a predefined set of rules; generating the categorized diagnostic models by learning the categorized learning data; and storing the categorized diagnostic models.

The categorizing of the learning data may involve categorizing the learning data based on at least one of patient information regarding each patient, medical institution information that made diagnoses, and imaging device information on imaging devices used to acquire diagnostic images.

The general aspect of the method may further involve generating an integrated diagnostic model based on the selected one or more diagnostic model.

The diagnosing of the lesion may involve: calculating model-by-model diagnosis result data by diagnosing the lesion of the patient based on each of the selected one or more diagnostic model; calculating a probability that the lesion is benign or malignant as integrated diagnosis result data by integrating the model-by-model diagnosis result data; and displaying both the model-by-model diagnosis result data and the integrated diagnosis result data.

The calculating of the integrated diagnosis result data may involve calculating the integrated diagnosis result data in consideration of preferences among the selected diagnostic models.

The general aspect of the method may further involve, after the diagnosing of the lesion: in response to the user changing selection of the selected one or more diagnostic model, diagnosing the lesion based on the changed selection.

In another general aspect, there is provided an apparatus for diagnosis, the apparatus including: a storage unit configured to store categorized diagnostic models, the categorized diagnostic models generated by categorizing learning data into categories and analyzing the categorized learning data; a model selection unit configured to select one or more diagnostic model for diagnosing a lesion from the categorized diagnostic models stored in the storage unit; and a diagnosis unit configured to diagnose the lesion based on lesion feature values obtained from image data of the lesion and the selected one or more diagnostic model.

The categorized diagnostic models stored in the model storage unit may be periodically updated.

Other features and aspects may be apparent from the following detailed description, the drawings, and the claims.

Figure 1:
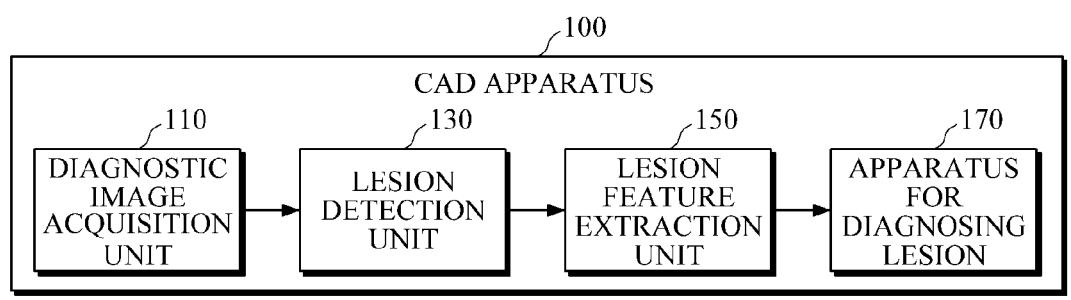
FIG. 1 is a block diagram illustrating an example of a computer-aided diagnosis (CAD) apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Although the processes illustrated and described herein include series of steps, it will be appreciated that these examples do not limit the methods described herein by the illustrated ordering of steps, as some steps may occur in different orders, some concurrently with other steps apart from that shown and described herein.

Unless otherwise defined, all terms, including technical and scientific terms, used herein have the same meaning as commonly understood by one of ordinary skill in the art to which this present disclosure belongs, consistent with the following description. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. Although some features may be described with respect to individual examples, aspects need not be limited thereto, and features from one or more examples may be combinable with other features from other examples.

Functional units, as described herein, are distinguished by their main functions. That is, two or more functional units can be integrated into fewer units, or a single functional unit can be divided into two or more smaller units. In addition, each functional unit may be configured to perform not only their main functions but also at least part of the main functions of other function units. Accordingly, each function unit, as described herein, should be interpreted as a functional entity, but not necessarily as a physical entity.

FIG. 1 is a diagram illustrating an example of a computer-aided diagnosis (CAD) apparatus.

Referring to FIG. 1, a CAD apparatus 100 may include a diagnostic image acquisition unit 110, a lesion detection unit 130, a lesion feature extraction unit 150 and an apparatus 170 for diagnosing lesion.

The diagnostic image acquisition unit 110 may acquire a diagnostic image of an affected part of a patient. In an example, the diagnostic image acquisition unit 110 may include one or more radiographic imaging apparatuses, ultrasonic imaging apparatuses, magnetic resonance imaging (MRI) apparatuses or computed tomography (CT) apparatuses.

The lesion detection unit 130 may detect the location and size of a lesion from the diagnostic image acquired by the diagnostic image acquisition unit 110. The lesion detection unit 130 may detect a lesion by using an automatic lesion detection algorithm or receiving information manually input by a user regarding the location of the lesion. For example, an MRI image of the chest may be obtained from a patient who is suspected of having a breast cancer.

In an example, the lesion feature extraction unit 150 may extract various features of a lesion, such as shape, margin, echo pattern, and the like, from the medical data acquired by the detection performed by the lesion detection unit 130. For example, an MRI image may be examined to extract lesion features such as an echo pattern of a neoplastic tissue. Further, the lesion features may be converted to quantitative lesion feature values.

The apparatus 170 may generate one or more categorized diagnostic models by which benign and malignant lesions can be distinguished from each other, by categorizing learning data into one or more categories and extracting and learning lesion features from learning data that belong to each of the categories. The apparatus 170 may determine whether a lesion of a patient to be diagnosed is benign or malignant based on the categorized diagnostic model and the features of the lesion detected by the lesion feature extraction unit 150. The term "learning data," as used herein, may indicate diagnostic image data obtained from a plurality of patients who are already diagnosed.

Figure 2:
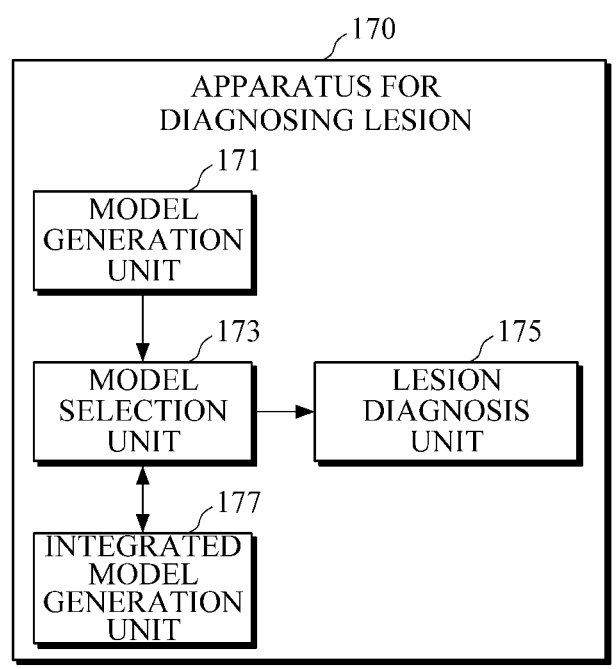
FIG. 2 is a block diagram illustrating an example of an apparatus for diagnosing lesion that uses categorized diagnostic models.

FIG. 2 is a diagram illustrating an example of an apparatus for diagnosing lesion using categorized diagnostic models.

Referring to FIG. 2, an apparatus for diagnosing lesion 170 may include a model generation unit 171, a model selection unit 173 and a diagnosis unit 175.

The model generation unit 171 may generate one or more categorized diagnostic models by categorizing learning data into one or more categories according to a predetermined set of rules and learning the categorized learning data in units of the categories, and may store the generated categorized diagnostic models.

In an example, the model generation unit 171 may categorize learning data into one or more categories based on patient information, medical institution information, and imaging device information. In this example, the patient information refers to information regarding each target patient, medical institution information refers to information regarding one or more medical institutions from which each target patient has been diagnosed, and imaging device information refers to information relating to imaging devices that was used to acquire diagnostic images of each target patient. The patient information may include a combination of anatomical and pathological features of each target patient, such as whether the patient has dense breasts or fatty breasts, as well as nonclinical information such as, for example, age, race and occupation of the patient. The medical institution information may include information on the name of hospitals or doctors, such as, for example, Samsung Medical Center, Asan Medical Center, and the like, from which the diagnosis of the target patient has been obtained. The imaging device information may include manufacturer information, such as Samsung Medison, Siemens, and the like, and model information of diagnostic imaging devices by which the diagnostic images of the target patient have been acquired.

The model generation unit 171 may generate one or more categorized diagnostic models by categorizing learning data based on the patient information, the medical institution information and the imaging device information and learning the categorized learning data. The model generation unit 171 may also generate a variety of diagnostic models by combining the categorized learning data in various manners and learning various combinations of the categorized learning data.

The model selection unit 173 may select one or more diagnostic models for the diagnosis of a new patient from among one or more categorized diagnostic models generated and stored by the model generation unit 171. In an example, the model selection unit 173 may categorize one or more categorized diagnostic models provided by the model generation unit 171 into one or more categories, may display the categorized diagnostic models in units of the categories, and may select one of the categorized diagnostic models in accordance with selection made by the user. The user may be a radiologist who is operating an apparatus for diagnosis lesion 170.

In another example, the model selection unit 173 may analyze information regarding the patient to be diagnosed or may analyze image data acquired from the patient, and may automatically search and find one or more categorized diagnostic models that is suitable for diagnosing the patient from all available categorized diagnostic models provided by the model generation unit 171, and may display the categorized diagnostic models found in the automatic search for the user. That is, the model selection unit 173 may search for and find one or more categorized diagnostic models that match, in terms of category, information extracted from patient information or medical image data stored in medical database (such as an electronic medical record (EMR) or personal health record (PHR) database) on the patient to be diagnosed, and may display the categorized diagnostic models found to match the extracted information. The model selection unit 173 may be configured to select one of the categorized diagnostic models found to match the extracted information automatically or to allow a user to select the categorized diagnostic models that the user wants to use in accordance with a selection made by the user.

The diagnosis unit 175 may perform an initial diagnosis of the lesion. For example, the diagnosis unit 175 may determine whether a lesion of the patient to be diagnosed is malignant or benign based on one or more categorized diagnostic models selected by the model selection unit 173 and lesion feature values extracted from acquired image data of the patient to be diagnosed. In an example, the diagnosis unit 175 may diagnose the lesion of the patient to be diagnosed by using each of the selected categorized diagnostic models, and may display the results of the diagnosis on a model-by-model basis. The diagnosis unit 175 may display the results of the diagnosis by marking the lesion of the patient to be diagnosed as malignant or benign on a display unit.

In another example, the diagnosis unit 175 may generate integrated diagnosis result data by integrating model-by-model diagnosis result data, which is obtained by using each of the selected categorized diagnostic models, and may display the integrated diagnosis result data. The integrated diagnosis result data may indicate the probability that the lesion of the patient to be diagnosed is malignant or benign. In this example, the diagnosis unit 175 may display both the model-by-model diagnosis result data and the integrated diagnosis result data together. In another example, the diagnosis unit 175 may calculate the integrated diagnosis result data by reflecting preferences among the selected categorized diagnostic models in the integration of the model-by-model diagnosis result data. The preferences among the selected categorized diagnostic models may be set and entered by the user, or may be set in such a manner that a higher preference level may be assigned to a diagnostic model that is frequently used and a lower preference level may be assigned to a diagnostic model that is less frequently used. Also, a high preference level may be assigned to a diagnostic model with a high precision compared to a diagnostic model with a low precision, or to a diagnostic model selected by the user than to a diagnostic model that is not selected by the user.

In an event that the user changes the selected one or more categorized diagnostic models to be used by a user choice, the diagnosis unit 175 may perform the lesion diagnosis again based on the newly selected categorized diagnostic models and display the results of the lesion diagnosis.

The apparatus for diagnosing lesion 170 may also include an integrated model generation unit 177.

The integrated model generation unit 177 may generate an integrated diagnostic model by one or more categorized diagnostic models selected by the model selection unit 173. In an example, the integrated model generation unit 177 may generate the integrated diagnostic model based on learning data from the selected categorized diagnostic models. In this example, the diagnosis unit 175 may perform lesion diagnosis by using the integrated diagnostic model, and may display the results of the lesion diagnosis.

Figure 3A:
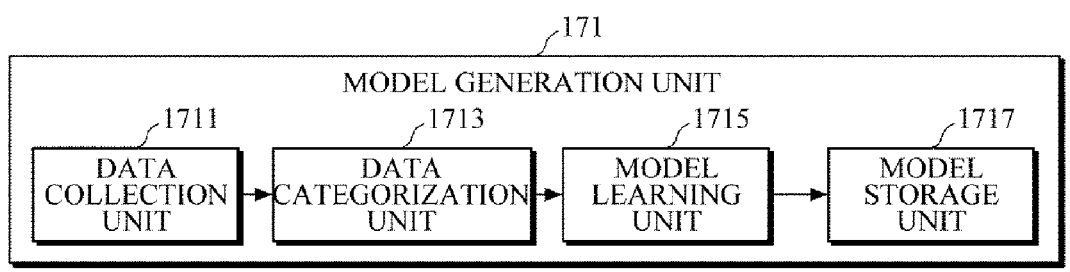
FIG. 3A is a block diagram of an example of a model generation unit.

FIG. 3A is a block diagram illustrating an example of the model generation unit 171 of FIG. 2.

Referring to FIG. 3A, the model generation unit 171 may include a data collection unit 1711, a data categorization unit 1713, a model learning unit 1715 and a model storage unit 1717.

The data collection unit 1711 may collect a large amount of learning data from one or more users or medical centers, from prior patients, or from a medical database. In an example, the data collection unit 1711 may receive diagnostic image data of a plurality of patients who are already diagnosed by a user or from an external medical database such as an EMR or PHR database, thereby collecting learning data for generating diagnostic models.

The data categorization unit 1713 may categorize the learning data collected by the data collection unit 1711 into one or more categories according to a predetermined set of rules.

In an example, the data categorization unit 1713 may categorize the collected learning data into one or more categories based on patient information, medical institution information and imaging device information of the collected learning data. The patient information may include anatomical or pathological features of each target patient, such as whether the patient has dense breasts or fatty breasts, and nonclinical information such as age, race and occupation. The medical institution information may include information on hospitals or doctors from which each target patient has been diagnosed, such as Samsung Medical Center, Asan Medical Center, and the like. The imaging device information may include manufacturer information, such as Samsung Medison, Siemens, and the like, and the serial number information of diagnostic imaging devices by which the diagnostic images of each target patient have been acquired. In the event that the collected learning data includes, for example, a diagnostic image of a patient acquired by Samsung Medison's imaging devices, the patient having dense breasts and the diagnosis being rendered by Samsung Medical Center, the collected learning data may be categorized as a "dense breasts" category, a "Samsung Medical Center" category and a "Samsung Medison" category, respectively.

The model learning unit 1715 may generate diagnostic models by learning categorized learning data provided by the data categorization unit 1713. In an example, the model learning unit 1715 may learn the categorized learning data by using, but is not limited to, a machine learning algorithm such as an artificial neural network, a decision tree, a genetic algorithm (GA), genetic programming (GP), Gaussian process regression, linear discriminant analysis (LDA), a K-nearest neighbor (K-NN) algorithm, a perceptron learning algorithm, a radial basis function network (RBFN), a support vector machine (SVM), and the like. That is, the model learning unit 1715 may use nearly all types of machine learning algorithms that categorize data by employing a model.

The model learning unit 1715 may generate a variety of diagnostic models by combining and learning the categorized learning data in various manners, and may generate a single integrated diagnostic model based on the whole categorized learning data.

The model storage unit 1717 may store the one or more categorized diagnostic models generated by the model learning unit 1715.

Figure 3B:
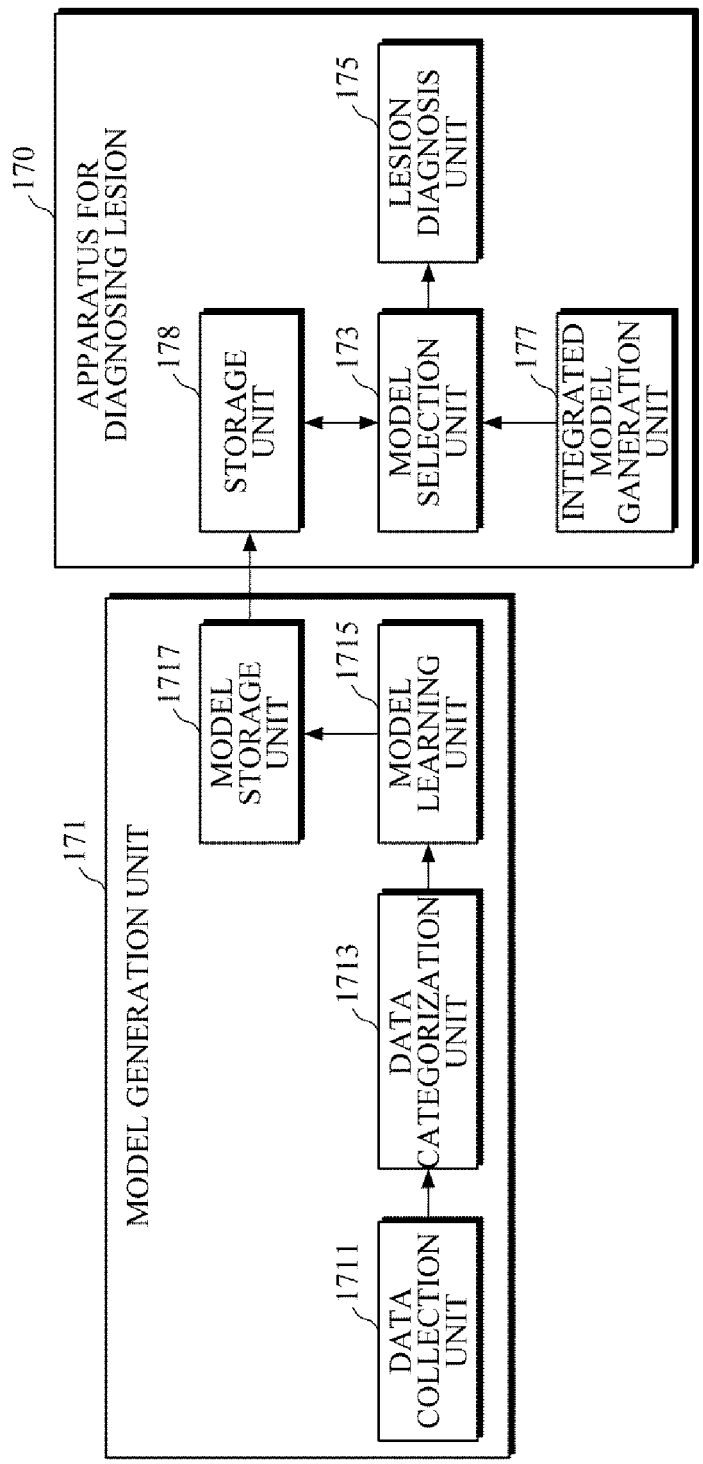
FIG. 3B is a block diagram illustrating an example of an apparatus for diagnosing lesion that uses models generated by a model generation unit.

Referring to FIG. 3B, in another example, a storage unit 178 may be included in an apparatus 170 for diagnosing lesion instead of a model generation unit 171 that includes a data collection unit 1711, a data categorization unit 1713, and a model learning unit 1715. For example, the categorized diagnostic models generated by analyzing categorized learning data may be stored in a model storage unit 1717 of a model generation unit 171, and a copy of the categorized diagnostic models may be stored in the storage unit 178 of an apparatus for diagnosing lesion 170. The model selection unit 173 and the diagnosis unit 175 of the apparatus for diagnosing lesion 170 may perform diagnosis by retrieving the stored categorized diagnostic models from storage unit 178 without performing the data categorization of the learning data performed by the model generation unit 171. The categorized diagnostic models may be stored in a memory or data storage of the apparatus for diagnosing lesion 170, and the stored categorized diagnostic models may be periodically or intermittently updated. For example, the apparatus for diagnosing lesion may include a hard drive, a drive for flash cards, or a removable memory unit, or have a wireless connection or hardwire connection to the model generation unit 171.

Figure 4A:
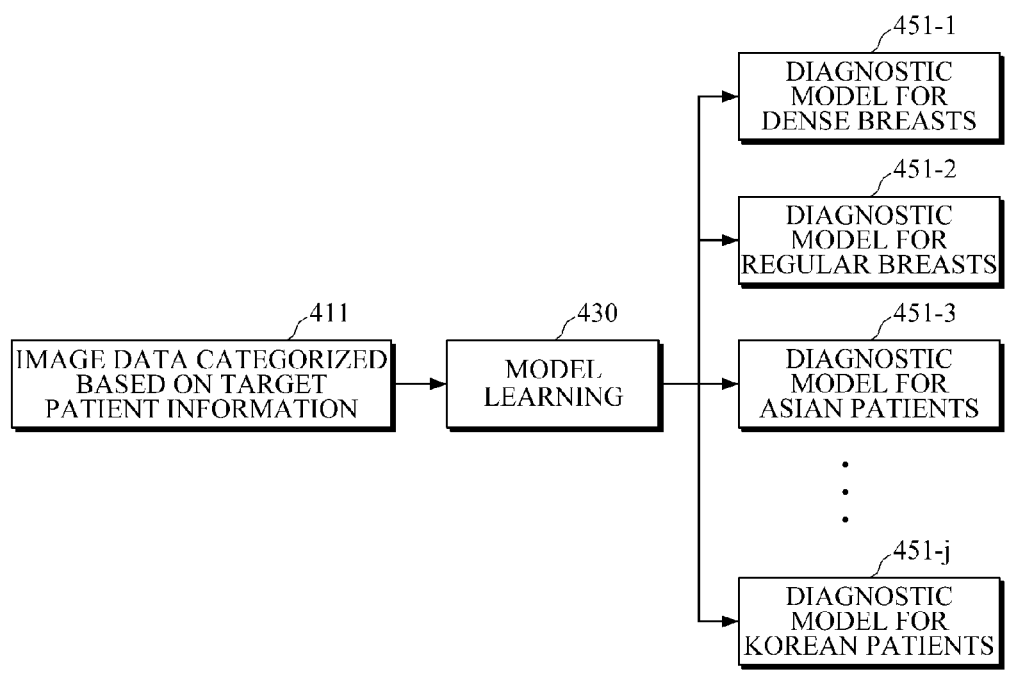
FIGS. 4A through 4C are diagrams illustrating an example of a method of generating categorized diagnostic models.
Figure 4B:
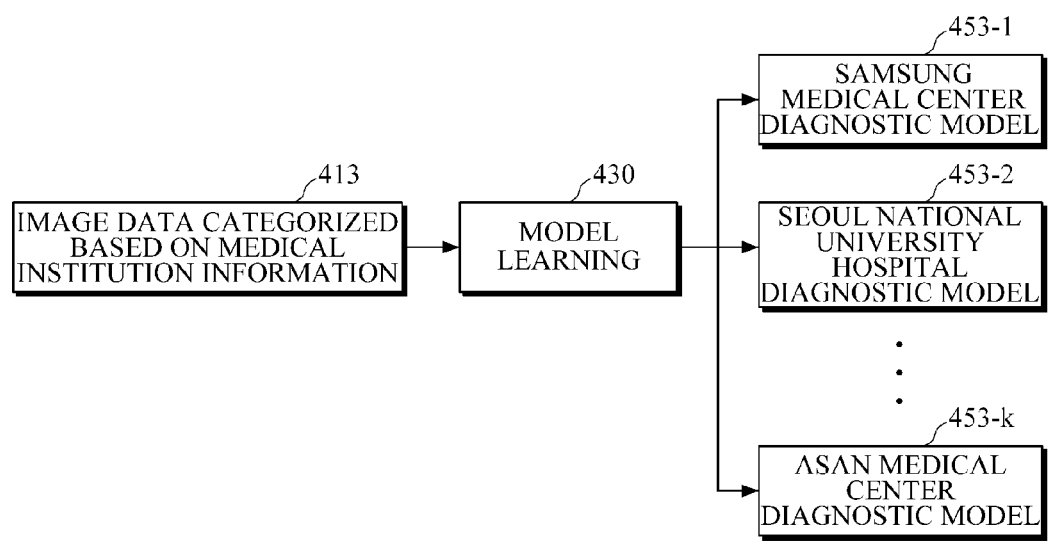
Figure 4C:
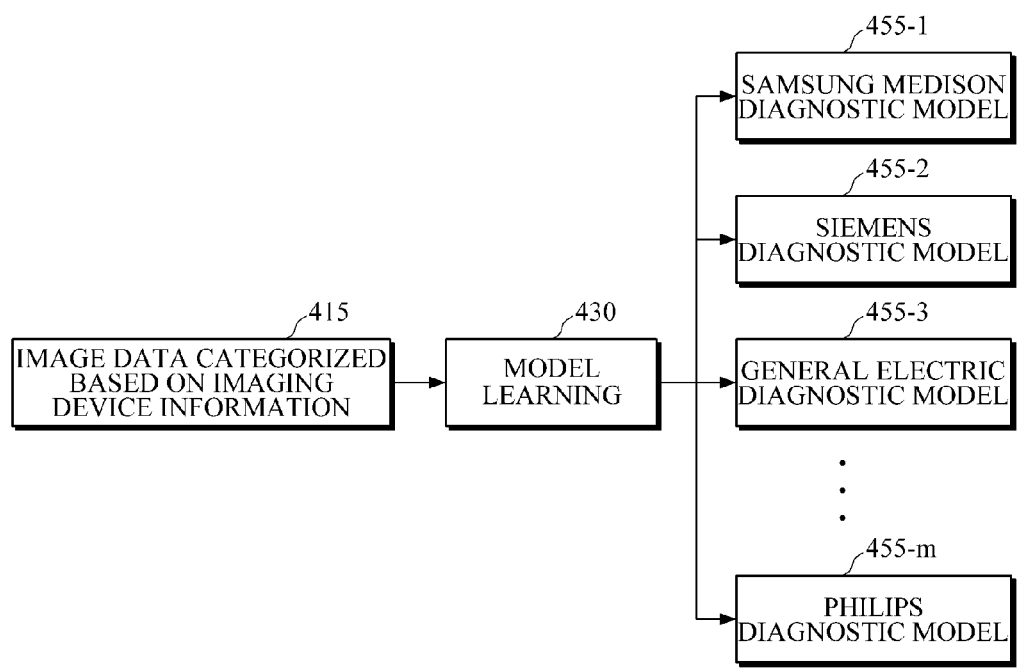

FIGS. 4A through 4C are diagrams illustrating examples of methods of generating categorized diagnostic models. For instance, FIG. 4A illustrates an example of a method of generating diagnostic models based on learning data that is categorized according to patient information. FIG. 4B illustrates an example of a method of generating diagnostic models based on learning data that is categorized according to medical institution information. FIG. 4C illustrates an example of a method of generating diagnostic models based on learning data that is categorized according to imaging device information.

Referring to FIG. 4A, the model generation unit 171 classifies a large amount of learning data based on patient information. The patient information may include anatomical or pathological features, such as whether the patient has dense breasts or regular breasts, and nonclinical information such as, for example, age, race and occupation. In an example, the large amount of learning data may be categorized into diagnostic image data for dense breasts, diagnostic image data for regular breasts, diagnostic image data for Asian patients, and diagnostic image data for Korean patients. By analyzing categorized image data 411 that is obtained by categorizing the large amount of learning data according to the patient information, using model learning 430, such as a machine learning algorithm, for example, the model generation unit 171 may generate various categorized diagnostic models. In this example, a diagnostic model 451-1 for diagnosing lesions in patients with dense breasts, a diagnostic model 451-2 for diagnosing lesions in patients with regular breasts or breast that are not dense, a diagnostic model 451-3 for diagnosing lesions in Asian patients, and a diagnostic model 451-*j* for diagnosing lesions in Korean patients, were generated by: learning categorized image data 411 that is obtained by categorizing the large amount of learning data according to the patient information and performing a model learning 430, such as, for example, the analysis of the categorized learning data using a machine learning algorithm.

Referring to FIG. 4B, the model generation unit 171 classifies a large amount of learning data based on medical institution information. The medical institution information may include information on hospitals or doctors from which each target patient has been diagnosed. In this example, the target patients in the learning data were diagnosed in Samsung Medical Center, Seoul National University, Asan Medical Center, and the like. In an example, the large amount of learning data may be categorized into Samsung Medical Center's diagnostic image data, Seoul National University Hospital's diagnostic image data, and Asan Medical Center's diagnostic image data. By learning the categorized image data 413 that is obtained by categorizing the large amount of learning data according to the medical institution information, and analyzing the categorized learning data by performing a model learning 430 such as, for example, a machine learning algorithm, the model generation unit 171 may generate various categorized diagnostic models. In this example, the categorized diagnostic models include, for example, a Samsung Medical Center diagnostic model 453-1 that reflects the diagnosis pattern of medical images collected from the Samsung Medical Center, a Seoul National University Hospital diagnostic model 453-2 that reflects the diagnosis pattern of medical images collected from the Seoul National University Hospital, and an Asan Medical Center diagnostic model 453-*k* that reflects the diagnosis pattern of medical images collected from the Asan Medical Center.

Referring to FIG. 4C, the model generation unit 171 classifies a large amount of learning data based on imaging device information. The imaging device information may include manufacturer information, such as Samsung Medison, and Siemens, and model names of diagnostic imaging devices by which diagnostic images of each target patient have been acquired. In an example, the large amount of learning data may be categorized into Samsung Medison's diagnostic image data, Siemens' diagnostic image data, General Electric's diagnostic image data and Phillips' diagnostic image data. By learning categorized image data 413 that is obtained by categorizing the large amount of learning data according to the imaging device information and applying a model learning 430, by performing, for example, a machine learning algorithm, the model generation unit 171 may generate various categorized diagnostic models. In this example, a Samsung Medison diagnostic model 455-1 that reflects diagnoses of images taken by Samsung Medison diagnostic imaging devices, a Siemens diagnostic model 455-2 that reflects diagnoses of images taken by Siemens diagnostic imaging devices, a General Electric diagnostic model 455-3 that reflects diagnoses of images taken by General Electric diagnostic imaging devices, and a Phillips diagnostic model 455-*m* that reflects diagnoses of images taken by Phillips diagnostic imaging devices are generated.

Figure 5:
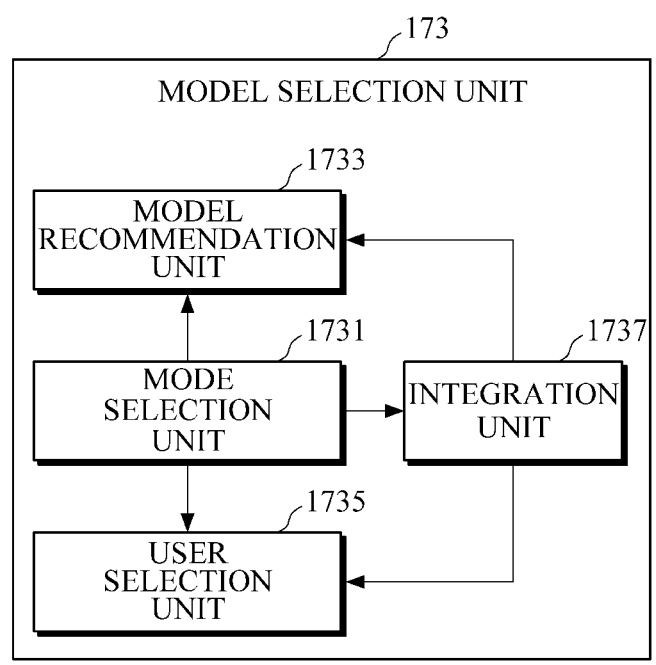
FIG. 5 is a block diagram of an example of a model selection unit.

FIG. 5 is a block diagram illustrating an example of the model selection unit 173.

Referring to FIG. 5, the model selection unit 173 may include a mode selection unit 1731, a model recommendation unit 1733, a user selection unit 1735 and an integration unit 1737.

The mode selection unit 1731 may allow the user to select or may automatically select one of an automatic recommendation mode, a user selection mode and an integrated mode. The automatic recommendation mode is a function of automatically searching for and recommending a diagnostic model suitable for each patient by analyzing information regarding each patient and/or analyzing acquired image data of each patient. The user selection mode is a function of allowing a user to directly choose a diagnostic model for each patient from one or more categorized diagnostic models generated by the model generation unit 171. The integrated mode is a function of enabling both the automatic recommendation mode and the user selection mode.

In response to the automatic recommendation mode being selected, the model recommendation unit 1733 may automatically search for and choose a diagnostic model suitable for each patient from one or more categorized diagnostic models by analyzing information regarding each patient and/or analyzing acquired image data of each patient. In an example, the model recommendation unit 1733 may select one or more diagnostic models that match information on a particular patient in terms of category as suitable diagnostic models for the particular patient. In this example, the suitable diagnostic models selected by the model recommendation unit 1733 may be displayed on, for example, a display screen, so as to allow a user to choose a diagnostic model therefrom.

In response to the user selection mode being selected, the user selection unit 1735 may display one or more categorized diagnostic models generated by the model generator 171 and may select one of the displayed diagnostic models as a suitable diagnostic model for each patient in accordance with selection made by a user.

In response to the integrated mode being selected, the integration unit 1737 may control both the model recommendation unit 1733 and the user selection unit 1735 to execute the automatic recommendation mode and the user selection mode, respectively. That is, the integration unit 1737 may control the model recommendation unit 1733 to automatically search for and choose a diagnostic model suitable for each patient from the categorized diagnostic models generated by the model generator 171 and may also control the user selection unit 1735 to display the categorized diagnostic models generated by the model generator 171 and to choose a diagnostic model suitable for each patient from the displayed diagnostic models in accordance with the selection made by a user.

Figure 6:
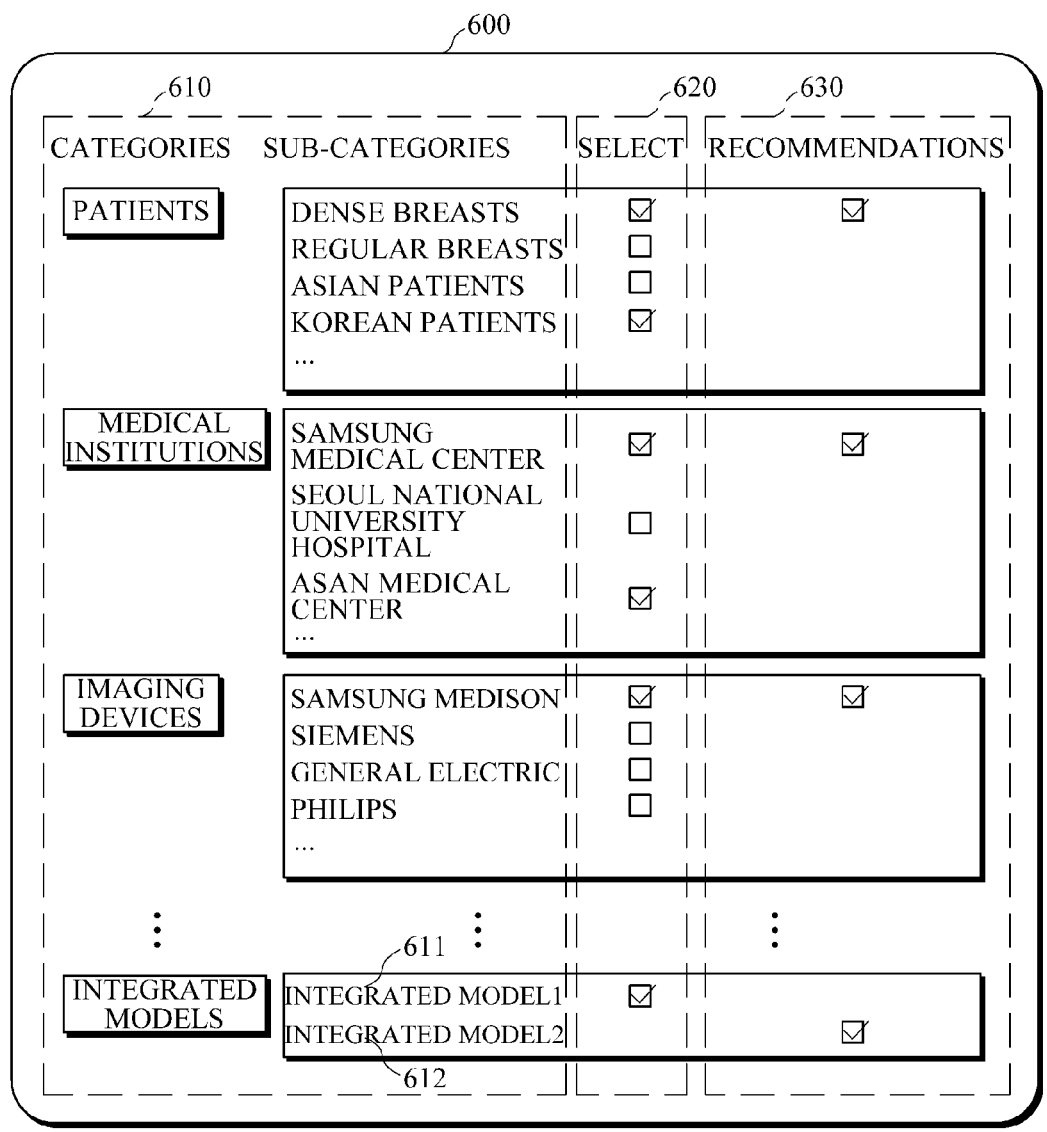
FIG. 6 is a diagram illustrating an example of a user interface (UI) screen for receiving a selection of diagnostic models from a user.

FIG. 6 is a diagram illustrating an example of a user interface (UI) screen for receiving a selection of a diagnostic model to be used from a user. In this example, it is assumed that the apparatus 170 is set to the integrated mode.

Referring to FIG. 6, a UI screen 600 may include a diagnostic model display region 610, a user selection display region 620 and a recommended model display region 630.

The diagnostic model display region 610 may display diagnostic models in units of categories. The categories may be obtained according to a set of rules for categorizing learning data. In the example illustrated in FIG. 6, a "patient" category, a "medical institution" category and an "imaging device" category are provided as main categories. The "patient" category includes a "dense breasts" category, a "regular breasts" category, an "Asian patients" category and a "Korean patients" category as sub-categories thereof. The "medical institution" category includes a "Samsung Medical Center" category, a "Seoul National University Hospital" category and an "Asan Medical Center" category as sub-categories thereof. The "imaging device" category includes a "Samsung Medison" category, a "Siemens" category, a "General Electric" category and a "Phillips" category as sub-categories thereof. However, the classification of diagnostic models is not limited to the example illustrated in FIG. 6, and may be performed in various manners.

The user selection display region 620 may receive a selection of a suitable diagnostic model for each patient, from among all the diagnostic models displayed in the diagnostic model display region 610, from a user. In the user selection region 620, a checkbox is provided for each of the displayed diagnostic models. Accordingly, the user may select each of the displayed diagnostic models simply by putting a check in the corresponding checkbox. However, the user may use various other methods than that set forth herein to choose a diagnostic model.

In the recommended diagnostic model display region 630, one or more diagnostic models that are determined as being suitable for the analysis of the diagnostic image of each patient based on an automatic search may be displayed. In an example, information or acquired image data of each patient may be analyzed, and one or more matching diagnostic models for each patient may be searched for, and the diagnostic models that match may be determined as recommended diagnostic models based on the results of the analysis. In this example, a checkbox may be provided for each of the recommended diagnostic models so that the user may select one of the recommended diagnostic models.

The diagnostic model display region 610 may also display one or more integrated models, i.e., first and second integrated models 611 and 612. Each of the first and second integrated models 611 and 612 may be generated based on one or more diagnostic models selected by the user. That is, each of the first and second integrated models 611 and 612 may be generated by learning all learning data used in the selected diagnostic models. The first integrated model 611 may be a diagnostic model obtained based on all learning data from one or more diagnostic models selected from the user selection region 620, i.e., a "dense breasts" diagnostic model, a "Korean Patients" diagnostic model, a "Samsung Medical Center" diagnostic model, an "Asan Medical Center" diagnostic model, and a "Samsung Medison" diagnostic model, and the second integrated model 612 may be a diagnostic model obtained based on all learning data from one or more diagnostic models selected from the recommended diagnostic model display region 630, i.e., the "dense breasts" diagnostic model, the "Samsung Medical Center" diagnostic model and the "Samsung Medison" diagnostic model.

Figure 7:
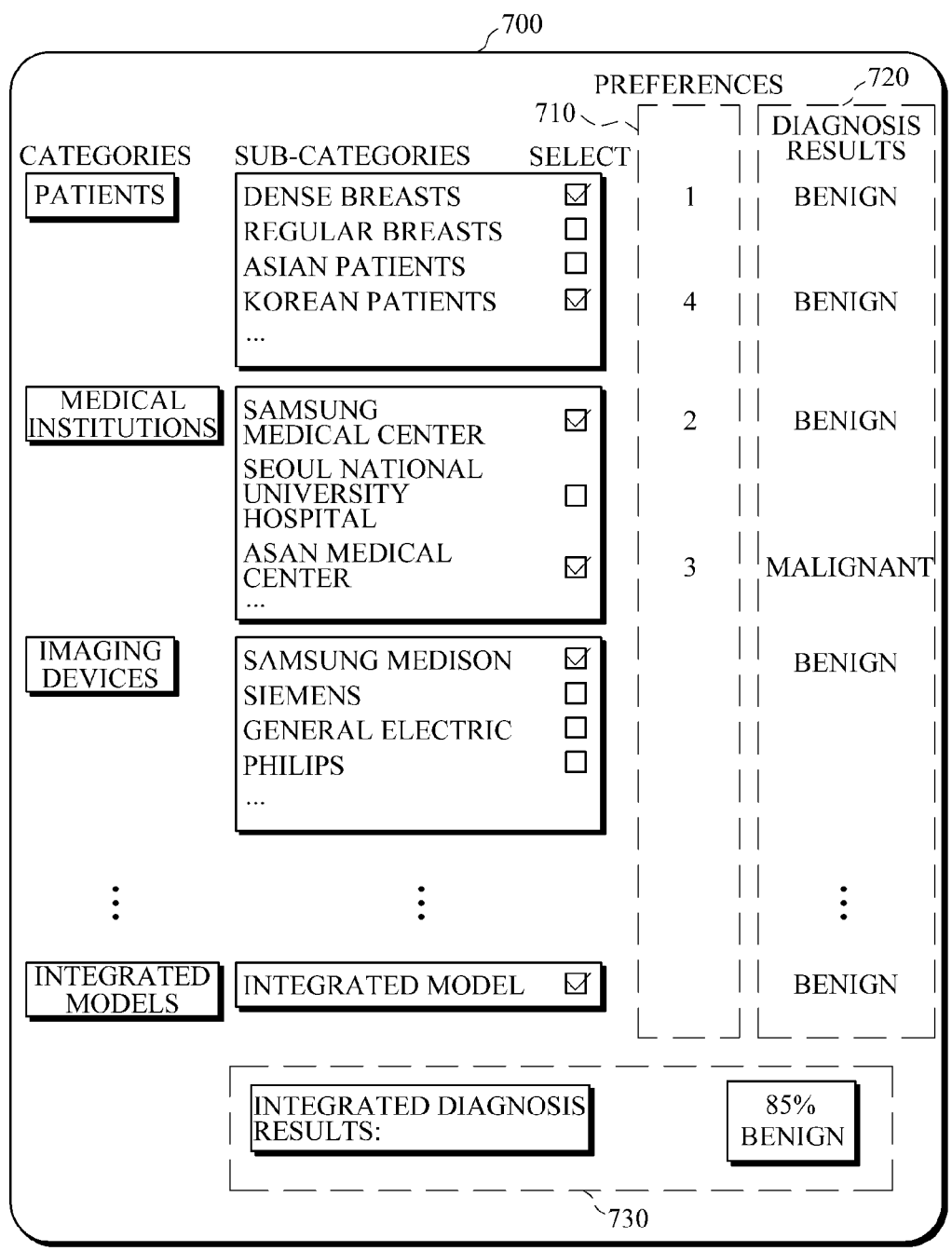
FIG. 7 is a diagram illustrating an example of a screen displaying the results of diagnosis.

FIG. 7 is a diagram illustrating an example of a screen displaying the results of lesion diagnosis. With respect to the description that follows, it is assumed that the apparatus 170 is set to the user selection mode.

Referring to FIG. 7, by using one or more diagnostic models selected by a user, the diagnosis unit 175 may diagnose a lesion of a patient whose diagnostic image is being examined. In this example, the patient to be diagnosed is referred to as a predetermined patient. In the example illustrated in FIG. 7, the diagnosis unit 175 may display both model-by-model diagnosis result data 720 that is obtained by diagnosing the lesion of the predetermined patient using each of the selected diagnostic models and integrated diagnosis result data 730 that is obtained by integrating the model-by-model diagnosis result data 720. In another example, the diagnosis unit 175 may display only the model-by-model diagnosis result data 720 or only the integrated diagnosis result data 730, without displaying the both result data.

The model-by-model diagnosis result data 720 and the integrated diagnosis result 730 may display whether the lesion of the patient is benign or malignant or may display the probability that the lesion of the patient is benign or malignant.

In an example, the integrated diagnosis result data 730 may be calculated by reflecting preferences 710 among the selected diagnostic models in the integration of the model-by-model diagnosis result data 720. The preferences 710 among the selected diagnostic models may be set and entered by a user, set by a default, or set in such a manner that a higher preference level may be assigned to a diagnostic model that is frequently used in comparison to a diagnostic model that is less frequently used. In the alternative, the references 710 may be set in such a manner that a higher preference level may be assigned to a diagnostic model with a high precision than to a diagnostic model with less higher precision, and/or in such a manner that a higher preference level may be assigned to a diagnostic model selected by the user in comparison to a diagnostic model that is not selected by the user. In other example, the preference level may be determined by giving consideration to any combination of the above described factors, such as the frequency of use, user selection, and precision of the diagnostic model.

In the example illustrated in FIG. 7, an integrated diagnostic model is obtained by integrating the "dense breasts" diagnostic model, the "Korean patients" diagnostic model, the "Samsung Medical Center" diagnostic model, the "Asan Medical Center" diagnostic model and the "Samsung Medison" diagnostic model. The integrated diagnostic result data 730 is calculated by assigning preference levels of 1, 2, 3 and 4 to the "dense breasts" diagnostic model, the "Samsung Medical Center" diagnostic model, the "Asan Medical Center" diagnostic model and the "Korean Patients" diagnostic model, respectively. By allowing the user to assign a high preference level for "dense breasts," the accuracy of the diagnosis proposed by the apparatus 170 can be further increased when medical data from patients who have dense breasts are analyzed.

Figure 8A:
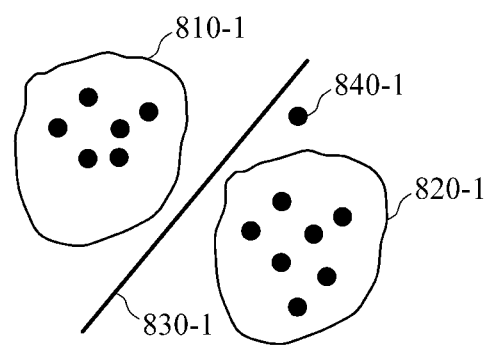
FIGS. 8A and 8B are diagrams illustrating an example of a method of performing diagnosis using diagnostic models obtained with a support vector machine (SVM).
Figure 8B:
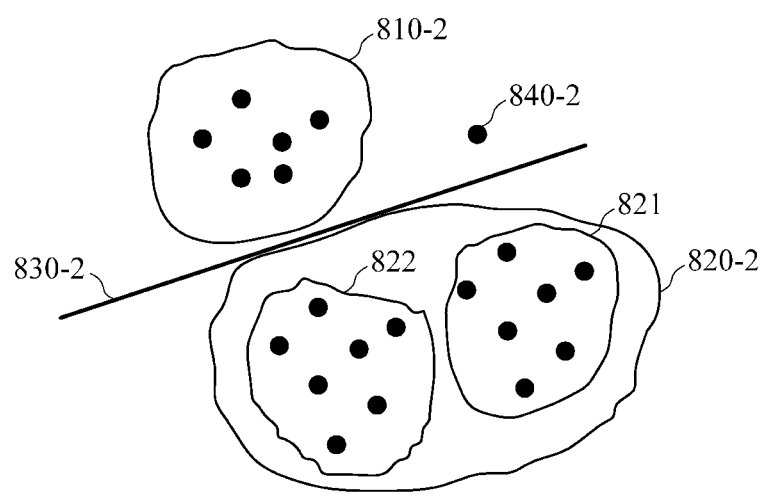

FIGS. 8A and 8B are diagrams illustrating examples of lesion diagnosis result data obtained by a diagnostic model established by using an SVM. More specifically, FIG. 8A is a diagram illustrating an example of the result obtained by performing a diagnosis of a lesion based on a diagnostic model established by learning diagnostic image data of individuals having dense breasts, and FIG. 8B is a diagram illustrating an example of the result obtained by performing a diagnosis of a lesion using a diagnostic model established by learning diagnostic image data of individuals having regular breasts.

Referring to FIG. 8A, a "dense breasts" diagnostic model is generated by receiving a large amount of diagnostic image data of a population of patients that have dense breasts. The patients may have been diagnosed as having either a benign or malignant lesion, and the features of lesion from the diagnostic image data may be used to calculate a hyperplane 830-1 on which a margin by which a benign group 810-1 and a malignant group 820-1 can be most suitably separated from each other. Feature values may be extracted from the diagnostic image data of a patient to be diagnosed, and a quantitative analysis may be performed to graphically or mathematically to depict the lesion feature values of the patient as image data 840-1. Again, the lesion feature values may relate to image-based information obtained from the diagnostic image data such as a shape, a margin, a density and the like of a lesion, for example, or values that are calculated or derived from the lesion features values extracted from the diagnostic image data.

In this example, the distance between the benign group 810-1 and the malignant group 820-1, is maximized.

In response to the receipt of image data 840-1 of a predetermined lesion to be diagnosed, it may be determined whether the predetermined lesion is benign or malignant by using the hyperplane 830-1. Since the image data 840-1 belongs to the malignant group 820-1 with respect to the hyperplane 830-1, the predetermined lesion may be diagnosed as malignant.

Referring to FIG. 8B, an integrated diagnostic model is generated by receiving a large amount of diagnostic image data for a population of patient who have dense breasts that are already diagnosed as benign or malignant and calculating based on the received diagnostic image data a hyperplane 830-2 on which a margin by which a benign group 810-2 and a malignant group 820-2 can be most suitably separated from each other. For example, the distance between the benign group 810-2 and the malignant group 820-2 is maximized. The malignant group 820-2 includes a malignant regular breast tissue group 822 and a malignant dense breast tissue group 821. In response to the receipt of image data 840-2 of a predetermined lesion to be diagnosed, it may be determined whether the predetermined lesion is benign or malignant by determining which side of the hyperplane 830-2 that image data 840-2 is located. Since the image data 840-2 belongs to the benign group 810-2 with respect to the hyperplane 830-2, the predetermined lesion may be diagnosed as benign.

Figure 9:
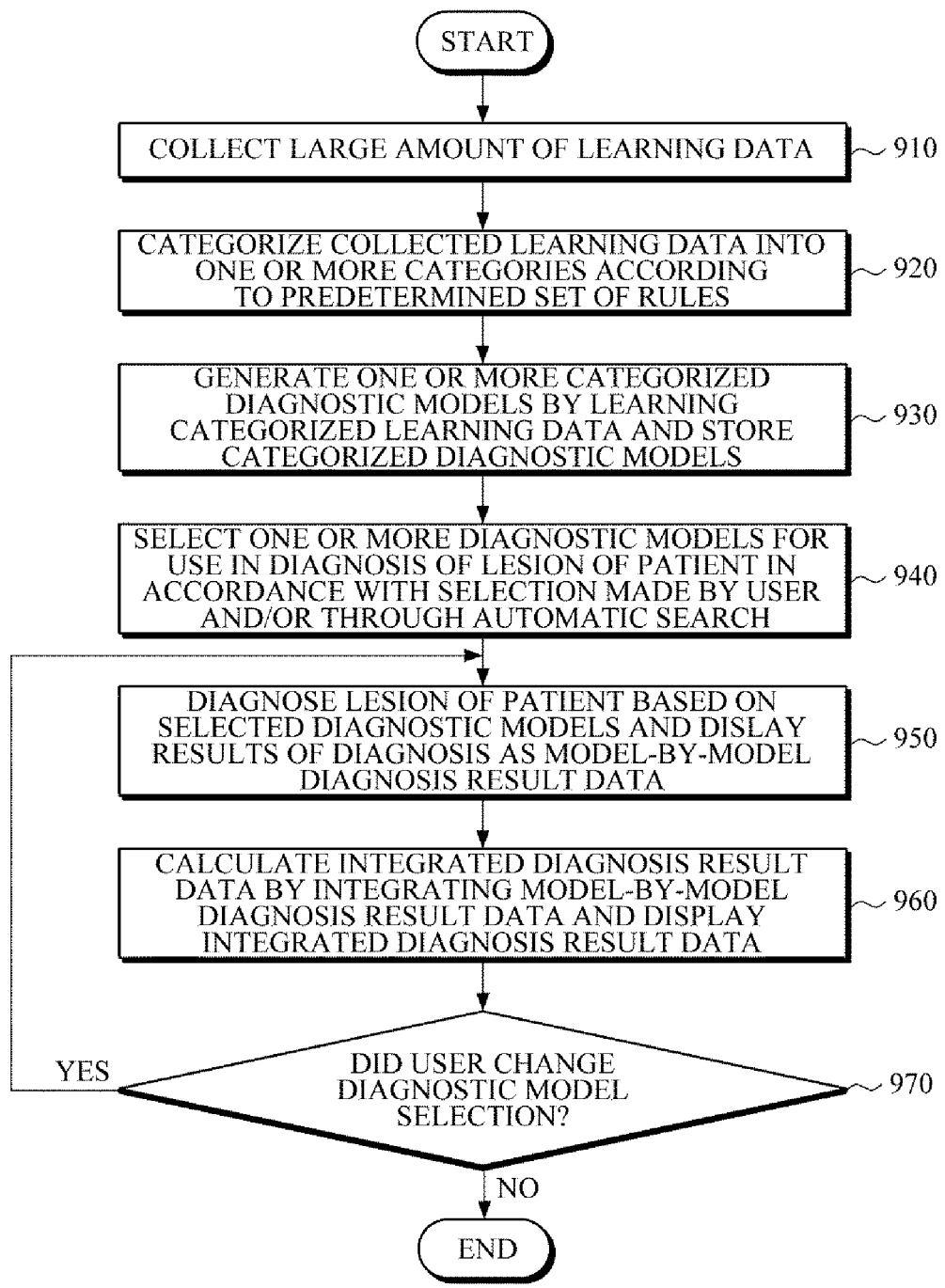
FIG. 9 is a flowchart illustrating an example of a method for diagnosis that uses categorized diagnostic models.

FIG. 9 is a flowchart illustrating an example of a method for diagnosing lesion by using categorized diagnostic models.

Referring to FIG. 9, a large amount of learning data is collected in 910. The term "learning data," as used herein, may indicate diagnostic image data acquired from a plurality of patients who are already diagnosed. The learning data may be collected from one or more users or from a medical database.

The collected learning data is categorized into one or more categories according to a predetermined set of rules in 920. In an example, the collected learning data may be categorized into one or more categories based on patient information, medical institution information and imaging device information of the collected learning data. The patient information may include anatomical or pathological features of each target patient, such as whether the target patient has dense breasts or non-dense breasts, and nonclinical information such as age, race and occupation of each target patient. The medical institution information may include information on hospitals or doctors from which each target patient has been diagnosed. For example, the hospital name may include Samsung Medical Center, Asan Medical Center, and the like. The imaging device information may include manufacturer information such as Samsung Medison, Siemens, and the like, and model names of diagnostic imaging devices by which diagnostic images of each target patient have been acquired.

A plurality of categorized diagnostic models is generated by learning the categorized learning data, and the generated categorized diagnostic models are stored in a data storage in 930. The categorized learning data may be learned by utilizing, but is not limited to, a machine learning algorithm such as an artificial neural network, a decision tree, a GA, GP, Gaussian process regression, LDA, a K-NN algorithm, a perceptron learning algorithm, an RBFN, an SVM, and the like. Nearly all types of machine learning algorithms that categorize data based on a model may be used to learn the categorized learning data.

One or more diagnostic models are selected to be used in the diagnosis from the categorized diagnostic models that are available in 940. In an example, suitable diagnostic models for diagnosis may be manually selected from the categorized diagnostic models by the user. In another example, the suitable diagnostic models for diagnosis may be automatically selected from the categorized diagnostic models by analyzing patient information or analyzing acquired image data of the predetermined patient.

The lesion of the predetermined patient is diagnosed by using each of the selected diagnostic models. The model-by-model diagnosis result data obtained by the diagnosis is displayed in 950. In an example, the model-by-model diagnosis result data may display whether the lesion of the predetermined patient is benign or malignant. In another example, the model-by-model diagnosis data may display the probability that the lesion of the predetermined patient is benign or malignant.

Integrated diagnosis result data is obtained by integrating the model-by-model diagnosis result data. The integrated diagnosis result is calculated and displayed in 960. In an example, the integrated diagnosis result data may be calculated by reflecting preferences among the selected categorized diagnostic models in the integration of the model-by-model diagnosis result data. The preferences among the selected categorized diagnostic models may be set and entered by the user. In the alternative, the preferences may be set in such a manner that a higher preference level may be assigned to a diagnostic model that is frequently used in comparison to a diagnostic model that is less frequently used. Also, the preferences may be set in such a manner that a higher preference level may be assigned to a diagnostic model with a high precision than to a diagnostic model with a lower precision, or a higher preference level may be assigned to a diagnostic model that is selected by the user in comparison to a diagnostic model that is not selected by the user.

The integrated diagnosis result data may display whether the lesion of the predetermined patient is benign or malignant or the probability that the lesion of the predetermined patient is benign or malignant.

In the event that the user changes the selection of the one or more diagnostic models manually as in 970, the lesion of the predetermined patient may be re-evaluated based on the changed selection of the diagnostic models, and the results of the diagnostic re-evaluation are displayed. The results of the diagnosis performed due to the reselection of the diagnostic models in 970 may be displayed by using the same method as used in 950 and 960 to display the model-by-model diagnostic result data and the integrated diagnostic result data.

Described above are various examples of apparatuses and methods for diagnosing lesion using categorized diagnostic models, which may be capable of enhancing the precision of diagnosis by presenting various diagnostic opinions to users by generating diagnostic models in consideration of the properties of data collected from various populations. Further, described above are various examples of methods of using the diagnostic model for diagnosing lesion.

Also described above are examples of an apparatus for diagnosing lesion by using categorized diagnostic models including: a model generation unit configured to categorize a large amount of learning data into one or more categories according to a predefined set of rules, generate one or more categorized diagnostic models by learning the categorized learning data, and store the categorized diagnostic models; a model selection unit configured to select one or more diagnostic models for diagnosing lesion of a patient from among the categorized diagnostic models; and a diagnosis unit configured to diagnose the lesion of the patient based on lesion feature values extracted from acquired image data of the patient and by using the selected diagnostic models.

Also described above are examples of an apparatus in which the model generation unit includes: a data collection unit configured to collect the large amount of learning data from one or more users or medical database; a data categorization unit configured to categorize the large amount of learning data into one or more categories according to the predefined set of rules; a model learning unit configured to generate the categorized diagnostic models by learning the categorized learning data; and a model storage unit configured to store the categorized diagnostic models.

Also described are the data categorization unit that may be further configured to categorize the large amount of learning data based on at least one of patient information, which is information on each target patient, medical institution information, which is information on one or more medical institutions from which each target patient has been diagnosed, and imaging device information, which is information on imaging devices by which diagnostic images of each target patient have been acquired.

The model selection unit may include: a model selector configured to select one of an automatic recommendation mode, a user selection mode and an integrated mode; a model recommendation unit configured to, in response to the automatic recommendation mode being selected, analyze information on or acquired image data of the patient, automatically search and find one or more diagnostic models that match the patient, in terms of category, based on the results of the analysis, and display the found diagnostic models; a user selection unit configured to, in response to the user selection mode being selected, choose at least one of the displayed diagnostic models in accordance with selection made by the user; and an integration unit configured to, in response to the integrated mode being selected, control both the model recommendation unit and the user selection unit to execute the automatic recommendation mode and the user selection mode, respectively.

An example of the apparatus may further include an integrated model generation unit configured to generate an integrated diagnostic model based on the selected diagnostic models. The diagnosis unit may be further configured to, in response to the model selection unit diagnosing the lesion of the patient using each of the selected diagnostic models, calculate and display model-by-model diagnosis result data based on the results of the diagnosis and calculate and display integrated diagnosis result data through integration of the model-by-model diagnosis result data, the integrated diagnosis result data displaying a probability that the lesion of the patient is benign or malignant. The apparatus may further include that the diagnosis unit is further configured to calculate and display the integrated diagnosis result data in consideration of preferences among the selected diagnostic models.

Also described above is an example of a method for diagnosing lesion by using categorized diagnostic models includes: categorizing a large amount of learning data into one or more categories according to a predefined set of rules, generating one or more categorized diagnostic models by learning the categorized learning data, and storing the categorized diagnostic models; selecting one or more diagnostic models for diagnosing lesion of a patient from among the categorized diagnostic models; and diagnosing the lesion of the patient based on lesion feature values extracted from acquired image data of the patient and by using the selected diagnostic models.

Various units as described herein may be implemented using hardware components. For example, the units may include a processing device, a display unit, a touch screen, a microprocessor, a memory, a data storage unit, and the like. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller, and a processor may be shared between two or more units.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored in one or more non-transitory computer readable recording mediums. A computer readable recording medium may include any data storage device, data storage unit or memory unit that can store data which can be thereafter read by a computer system or processing device. Examples of the computer readable recording medium include read-only memory (ROM), random-access memory (RAM), CD-ROMs, magnetic tapes, floppy disks, optical data storage devices. Also, functional programs, codes, and code segments for accomplishing the examples disclosed herein can be easily construed by programmers skilled in the art to which the examples pertain based on and using the flow diagrams and block diagrams of the figures and their corresponding descriptions as provided herein.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for diagnosing lesions, the apparatus comprising:
a memory; and
at least one processor configured to:
categorize learning data into one or more categories,
generate one or more categorized diagnostic models based on the categorized learning data,
select one or more diagnostic models from the categorized diagnostic models,
diagnose the lesion based on image data of the lesion and the selected one or more diagnostic models,
analyze, in response to activation of an automatic recommendation mode, patient information or image data of a patient to determine one or more diagnostic models to diagnose the lesion, and display the one or more determined diagnostic model,
allow, in response to activation of a user selection mode, selection of at least one of the categorized diagnostic model, and
execute, in response to activation of an integrated mode, the automatic recommendation mode and the user selection mode, respectively.

2. The apparatus of claim 1, wherein the at least one processor is further configured to diagnose the lesion based on lesion feature values extracted from the image data and the selected one or more diagnostic models.

3. The apparatus of claim 1, wherein the at least one processor is further configured to:
collect the learning data from prior patients or medical database;
categorize the learning data into the one or more categories according to a predefined set of rules;
generate the categorized diagnostic models by learning the categorized learning data; and
store the categorized diagnostic models in the memory.

4. The apparatus of claim 3, wherein the at least one processor is further configured to categorize the learning data based on at least one of patient information regarding each patient, medical institution information that made diagnoses, or imaging device information on imaging devices used to acquire diagnostic images.

5. The apparatus of claim 1, wherein the at least one processor is further configured to:
generate an integrated diagnostic model based on the selected one or more diagnostic models.

6. The apparatus of claim 1, wherein the at least one processor is further configured to:
calculate and display model-by-model diagnosis result data based on the diagnosis, and
calculate and display integrated diagnosis result data through integration of the model-by-model diagnosis result data,
wherein the integrated diagnosis result data is displayed as a probability that the lesion is benign or malignant.

7. The apparatus of claim 6, wherein the at least one processor is further configured to calculate and display the integrated diagnosis result data in consideration of preferences among the selected diagnostic models.

8. A method for diagnosing lesions comprising:
generating, using a model generator configured to categorize data into one or more categories, one or more categorized diagnostic models based on the categorized learning data;
selecting, using a model selection processor configured to select diagnostic models, one or more diagnostic models from the categorized diagnostic models; and
diagnosing, the lesion based on image data of the lesion and the selected one or more diagnostic models,
wherein the selecting of the one or more diagnostic models comprises:
analyzing, in response to activation of an automatic recommendation mode, patient information or image data of a patient to determine the one or more diagnostic models to diagnose the lesion, and displaying the one or more determined diagnostic models,
allowing, in response to activation of a user selection mode, selection of at least one of the categorized diagnostic models, and
activating, in response to activation of an integrated mode, the automatic recommendation mode and the user selection mode to execute respectively the automatic recommendation mode and the user selection mode.

9. The method of claim 8, wherein the diagnosing of the lesion comprises diagnosing the lesion based on lesion feature values extracted from the image data and the selected one or more diagnostic models.

10. The method of claim 8, wherein the generating of the categorized diagnostic models comprises:
collecting the learning data from prior patients or a medical database;
categorizing the learning data into the one or more categories according to a predefined set of rules;
generating the categorized diagnostic models by learning the categorized learning data; and
storing the categorized diagnostic models.

11. The method of claim 10, wherein the categorizing of the learning data comprises categorizing the learning data based on at least one of patient information regarding each patient, medical institution information that made diagnoses, or imaging device information on imaging devices used to acquire diagnostic images.

12. The method of claim 8, further comprising:
generating an integrated diagnostic model based on the selected one or more diagnostic models.

13. The method of claim 8, wherein the diagnosing of the lesion comprises:
calculating model-by-model diagnosis result data by diagnosing the lesion of the patient based on each of the selected one or more diagnostic models;
calculating a probability that the lesion is benign or malignant as integrated diagnosis result data by integrating the model-by-model diagnosis result data; and
displaying both the model-by-model diagnosis result data and the integrated diagnosis result data.

14. The method of claim 13, wherein the calculating of the integrated diagnosis result data comprises calculating the integrated diagnosis result data in consideration of preferences among the selected diagnostic models.

15. The apparatus of claim 1, wherein the at least one processor is further configured to store categorized diagnostic models in the memory.

16. The apparatus of claim 15, wherein the categorized diagnostic models stored in the memory are periodically updated.

* * * * *